(12) United States Patent
Mcrae et al.

(10) Patent No.: US 12,104,134 B2
(45) Date of Patent: Oct. 1, 2024

(54) APPARATUS AND PROCESS FOR CATALYZED STEAM BIOFUEL PRODUCTION

(71) Applicant: Kitsault Energy, Ltd., Ottawa (CA)

(72) Inventors: Glenn Aldon Mcrae, Ottawa (CA); Alexis Fosse Mackintosh, Vancouver (CA); Onita Debbie Basu, Ottawa (CA); Margaret Anne Knowlings, Vancouver (CA)

(73) Assignee: Kitsault Energy, Ltd., Ottawa (CA)

( * ) Notice: Subject to any disclaimer, the term of this patent is extended or adjusted under 35 U.S.C. 154(b) by 0 days.

(21) Appl. No.: 17/924,467

(22) PCT Filed: May 6, 2021

(86) PCT No.: PCT/CA2021/050634
§ 371 (c)(1),
(2) Date: Nov. 10, 2022

(87) PCT Pub. No.: WO2021/226703
PCT Pub. Date: Nov. 18, 2021

(65) Prior Publication Data
US 2023/0340350 A1 Oct. 26, 2023

Related U.S. Application Data

(60) Provisional application No. 63/023,050, filed on May 11, 2020.

(51) Int. Cl.
*C07C 51/42* (2006.01)
*B01J 19/00* (2006.01)
(Continued)

(52) U.S. Cl.
CPC ............ *C10L 9/086* (2013.01); *B01J 19/0006* (2013.01); *B01J 19/0053* (2013.01);
(Continued)

(58) Field of Classification Search
CPC .. B01J 19/0006; B01J 19/0053; B01J 19/245; B01J 2219/0004; B01J 2219/00051;
(Continued)

(56) References Cited

U.S. PATENT DOCUMENTS

| 8,715,462 B2 | 5/2014 | Mackintosh |
| 9,683,328 B2 | 6/2017 | Mackintosh |
| 2019/0367814 A1 | 12/2019 | Brandhorst, Jr. et al. |

FOREIGN PATENT DOCUMENTS

| CA | 2740225 A1 * | 5/2010 | .......... B01J 19/0006 |
| CA | 2900092 A1 | 8/2014 | |
| WO | WO-2014122163 A1 * | 8/2014 | ................ C10L 5/08 |

OTHER PUBLICATIONS

Ghaziaskar, Amin et al, ("Catalyzed Hydrothermal Carbonization with Process Liquid Recycling", Energy Fuels 2019, 33, p. 1167-1174 (Year: 2019).*

(Continued)

*Primary Examiner* — Ellen M McAvoy
*Assistant Examiner* — Chantel Graham
(74) *Attorney, Agent, or Firm* — Stevens & Showalter LLP

(57) ABSTRACT

A method and apparatus for producing a solid biofuel from hydrocarbonaceous feedstock is described. The process includes loading a hydrocarbonaceous feedstock into a reactor vessel, adding an aqueous catalyst solution into the reactor vessel, wherein the catalyst solution resides at the bottom of the reactor vessel under the hydrocarbonaceous feedstock position, heating the reactor vessel at or above 170° C. to catalyze a reaction of hydrocarbonaceous feedstock under saturated steam conditions for a time sufficient to yield a polymeric biofuel, and isolating the polymeric biofuel from the reactor vessel.

26 Claims, 8 Drawing Sheets

(51) Int. Cl.
*B01J 19/24* (2006.01)
*C07D 307/48* (2006.01)
*C07D 307/50* (2006.01)
*C10L 5/44* (2006.01)
*C10L 9/08* (2006.01)

(52) U.S. Cl.
CPC .............. *B01J 19/245* (2013.01); *C07C 51/42* (2013.01); *C07D 307/48* (2013.01); *C07D 307/50* (2013.01); *C10L 5/442* (2013.01); *B01J 2219/0004* (2013.01); *B01J 2219/00051* (2013.01); *B01J 2219/00162* (2013.01); *C10L 2200/0469* (2013.01); *C10L 2290/06* (2013.01); *C10L 2290/08* (2013.01); *C10L 2290/141* (2013.01); *C10L 2290/146* (2013.01); *C10L 2290/28* (2013.01)

(58) Field of Classification Search
CPC .............. B01J 2219/00162; B01J 19/24; B01J 19/2425; C07C 51/42; C07C 51/00; C07C 53/02; C07C 53/08; C07C 59/185; C07D 307/48; C07D 307/50; C10L 2200/0469; C10L 2290/06; C10L 2290/08; C10L 2290/141; C10L 2290/146; C10L 2290/28; C10L 5/442; C10L 9/086; C10L 2290/24; C10L 5/403; C10L 5/42; C10L 5/445; C10L 5/46; Y02E 50/30; Y02E 50/10
See application file for complete search history.

(56) References Cited

OTHER PUBLICATIONS

Titirici, Maria-Magdalena et al. "Back in the black: hydrothermal carbonization of plant material as an efficient chemical process to treat the CO2 problem?"; New J. Chem., 2007, 31, 787-789.
Ghaziaskar, Amin et al. "Catalyzed Hydrothermal Carbonization with Process Liquid Recycling"; Energy Fuels, 2019, 33, 1167-1174.
Ghaziaskara et al. "Production of Organic Compounds through Catalyzed Hydrothermal Carbonization of Woody Biomass"; Energy Fuels, 2019, 33, 10, 9879-9885.
Mackintosh, Alexis et al. "Hydrothermal Polymerization Catalytic Process Effect of Various Organic Wastes on Reaction Time, Yield, and Temperature"; Processes, 2020, 8, 303.
International Search Report and Written Opinion of the International Searching Authority dated Aug. 9, 2021; International Application No. PCT/CA2021/050634; Canadian Intellectual Property Office; Gatineau, Quebec.
Notification of the Recording of a Change dated Nov. 16, 2022; International Application No. PCT/CA2021/050634; Canadian Intellectual Property Office; Gatineau, Quebec.

\* cited by examiner

APPARATUS AND PROCESS FOR CATALYZED STEAM BIOFUEL PRODUCTION

FIELD OF THE INVENTION

This invention relates to preparation of biofuels, and more particularly, to a novel catalyzed steam hydro-thermalization process in a compact bioreactor utilizing a volatile catalyst, or a steam hydro-thermalization process without use of catalyst, that turns wet wood into a polymeric high-energy density solid biofuel, as well as can produce other valuable organic chemicals.

BACKGROUND

Biofuel is a type of fuel that is derived from a renewable source, such as a biomass, which is typically comprised of plant or algae material, unlike fossil fuels such as petroleum, coal, and natural gas. Further, a biomass can be converted directly into biofuels. Fuels derived from a biomass have zero net carbon dioxide ($CO_2$) emissions if produced without the use of fossil fuels. As such, they have been touted as possible replacements for fossil fuels, such as substitutes for coal and oil.

As a result of the potential benefits of biofuels, research concerning the process of converting a biomass into biofuels is continuously evolving. For example, U.S. Pat. No. 8,715,462 B2 to Mackintosh, incorporated herein by reference in its entirety, discloses methods and an apparatus for exploiting coated paper products, such as coated paper cups, to produce products including biofuels having a high energy density. Such biofuels may, in turn, be mixed with coal or other suitable fuels that have good binding characteristics. In some embodiments, useful chemicals, such as 2,5-(hydroxymethyl)-furfural (HMF), are produced. The methods utilized for the production of such fuels typically involves a heat treatment at relatively mild temperatures and pressures under acidic conditions. The residual solids have an excellent energy density and can be burned as a green replacement for coal or other fuels. The energy density of the residual solids can be on the order of 27 to 30 GJ/Tonne. The residual solids may be pelletized for use as a fuel, used as a binder in pelletizing coal or other fuels, and/or mixed with coal or other fuels to provide blended fuels.

Further, U.S. Pat. No. 9,683,328 to Mackintosh, incorporated herein by reference in its entirety, discloses a method of preparation of biofuels and other useful products, such as HMF. The disclosed method produces a solid biofuel from a feedstock that includes a polysaccharide, hemicellulose, cellulose and lignin or a combination thereof. The method includes the steps of providing an aqueous slurry of the feedstock, making the slurry acidic, and cooking the slurry at a temperature in the range of about 170° C. to 300° C. and a suitable pressure, such as in a pressure exceeding the atmospheric pressure for a suitable amount of time so as to cause one or more of the polysaccharide, hemicellulose, cellulose and lignin to react and yield solid hydrophobic polycarbon compounds comprising polycyclic derivatives of HMF.

The research article by Mackintosh et al. titled, "Hydrothermal Polymerization Catalytic Process Effect of Various Organic Wastes on Reaction Time, Yield, and Temperature," *Processes* 2020, 8, 303, incorporated herein by reference in its entirety, discloses optimizing the hydrothermal polymerization (HTP) catalytic process conditions (temperature, pressure, process time, yield rate) for the conversion of biomass to a high-energy-density biofuel using an acid-based catalyst. This study illustrates that the HTP catalytic process for a reference feedstock lowers the temperature by between 10° C. and 40° C., reduces the pressure requirement by one (1) MPa to two (2) MPa, increases the yield by 22%, and shortens the total processing time by up to three (3) hours when compared with the conventional hydrothermal carbonization (HTC) process.

The research article by Ghaziaskara et al., "Catalyzed Hydrothermal Carbonization with Process Liquid Recycling" *Energy Fuels* 2019, 33, 2, 1167-1174, incorporated herein by reference in its entirety, discloses the production of organic compounds through Catalyzed Hydrothermal Carbonization (CHTC) of woody biomass thereby producing biofuel, also known as hydrochar, and valuable aqueous products (VAPs) that could potentially be harvested to facilitate commercialization of the process. The article further discloses a CHTC method to produce hydrochar biofuel from wood chips at a temperature of about 240° C. in one (1) hour from batches that includes recycling of the process liquid. The CHTC process with recycling may provide a green hydrochar biofuel with excellent handling, storage, and transportation properties suitable as a direct replacement for coal.

Additionally, another research article by Ghaziaskara et al., "Production of Organic Compounds through Catalyzed Hydrothermal Carbonization of Woody Biomass", *Energy Fuels,* 2019, 33, 10, 9879-9885, incorporated by reference herein in its entirety, discloses that both the energy yield and the mass yield increase as the liquid-to-biomass ratio decreases, see for example, FIG. 2c in the article. This result suggests that the yield of a solid biofuel can be increased through the reduction in the amount of water used in the process.

U.S. Patent Application No. 2019/0367814A1 to Brandhorst, JR. et al., incorporated herein by reference in its entirety, discloses a process for utilizing thermolysis methods to convert various treated wood sources into a clean fuel gas and biochar. The process involves inputting a treated wood waste source into a thermolysis system, wherein the thermolysis system includes a primary reactor and at least a secondary reactor, the reactors having a process temperature between about 300° C. and 1000° C., and generating outputs of the thermolysis system including clean fuel gas and biochar.

However, the processes, referred to above, for converting wood/biomass into biofuel are inefficient and not economical because they employ a liquid catalyzed process that require large quantities of water and a large biofuel reactor. Additionally, they require large amounts of energy and post-processing cleanup.

Thus, an economical, efficient process for the production of useful biofuels and related compounds from a renewable source, such as a solid biomass and/or wood addressing the aforementioned needs is desired.

SUMMARY OF INVENTION

Embodiments of an improved catalyzed steam hydrothermalization carbonization process that turns wet wood into a polymeric high-energy-density biofuel includes the steps of loading a hydrocarbonaceous feedstock into a reactor vessel, adding an aqueous catalyst solution into the reactor vessel, wherein the catalyst solution resides at the bottom of the reactor vessel under the hydrocarbonaceous feedstock position, heating the reactor vessel to a suitable temperature, such as to a temperature of at least 170° C., to catalyze the reaction of hydrocarbonaceous feedstock under saturated steam conditions for a time sufficient to yield polymeric biofuel, and isolating the biofuel from the reactor vessel. It is to be noted that the reaction process rate of reaction is typically dependent on three principal factors: (1) the temperature; (2) the time of reaction; and (3) the concentration/strength of the catalyst. As such, a stronger catalyst would likely require less time than a weaker catalyst. Further, an increase in reaction temperature would likely decrease the amount of time required for the reaction to go to completion (i.e., the reaction is faster at higher temperatures), while a decrease in the temperature would likely increase the amount of time required for the reaction to go to completion (i.e., the reaction is slower at lower temperatures).

Other embodiments include a method of producing a solid biofuel from hydrocarbonaceous feedstock including the steps of loading a hydrocarbonaceous feedstock into a reactor vessel, introducing saturated steam comprising a catalyst into the reactor vessel, heating the reactor vessel to a suitable temperature, such as a temperature of at least 170° C., to catalyze the reaction of hydrocarbonaceous feedstock under saturated steam conditions for a time sufficient to yield polymeric biofuel, and optionally isolating the aqueous solution containing valuable organic chemicals from the reactor vessel. Other embodiments can also include a method of producing a solid biofuel from hydrocarbonaceous feedstock including the steps of loading a hydrocarbonaceous feedstock into a reactor vessel, introducing water in the form of saturated steam, without a catalyst, into the reactor vessel, heating the reactor vessel to a suitable temperature, such as a temperature of at least 170° C., to cause or promote the reaction of hydrocarbonaceous feedstock under saturated steam conditions for a time sufficient to yield polymeric biofuel, and optionally isolating the aqueous solution containing valuable organic chemicals from the reactor vessel.

Embodiments of apparatuses and systems for producing biofuel include at least one reactor vessel, a removable basket positioned in the reactor vessel for holding the hydrocarbonaceous material, the removeable basket being positioned, such as being supported on a metal support, above the bottom of the reactor vessel, a heater for heating the reactor vessel, a cover, such as a lid cover, on the reactor vessel configured for inputting hydrocarbonaceous feedstock and outputting biofuel or a reaction product from the reactor vessel. The apparatus for producing biofuel may further include a plurality of reaction vessels in communication with each other.

These and other features of the present invention will become readily apparent upon further review of the following specification and drawings.

DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
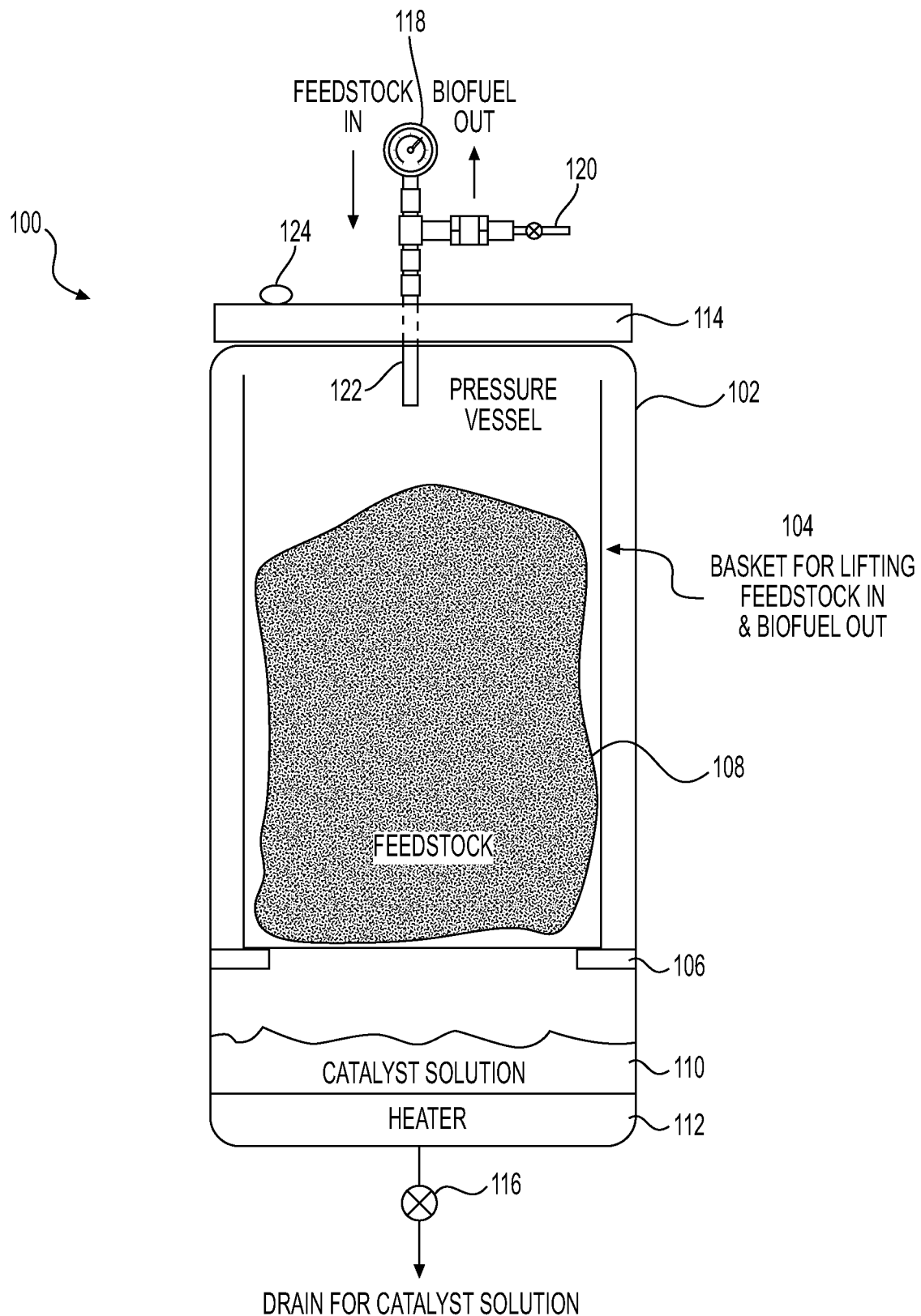
FIG. 1 is a side sectional view of an embodiment of a reactor vessel, according to the present invention.

The present disclosure relates to embodiments of methods for producing a solid biofuel from hydrocarbonaceous feedstock and to embodiments of apparatuses for producing the biofuel. An embodiment of a method for producing a solid biofuel from hydrocarbonaceous feedstock includes the steps of loading a hydrocarbonaceous feedstock into a reactor vessel, introducing steam comprising a catalyst into the reactor vessel, heating the reactor vessel to a suitable temperature, such as to a temperature of at least 170° C., to catalyze the reaction of hydrocarbonaceous feedstock under saturated steam conditions for a time sufficient to yield polymeric biofuel, and isolating the liquid products from the reactor vessel. The temperature for the reaction process will typically depend on various factors, such as the time for the reaction, reaction rate, type and amount of biofuel used, for example, as can depend on the use or application, and should not be construed in a limiting sense. Desirably, a temperature of at least 170° C. is typically a practical temperature where the biofuel reaction can occur at a reaction rate that is economic for biofuel production. It is to be noted that the reaction process rate of reaction is typically dependent on the three principal factors: (1) the temperature; (2) the time of reaction; and (3) the concentration/strength of the catalyst. As such, a stronger catalyst would likely require less time than a weaker catalyst for the reaction process. Further, an increase in reaction temperature would likely decrease the amount of time required for the reaction to go to completion (i.e. the reaction rate increases with temperature), while a decrease in the temperature would likely increase the amount of time required for the reaction to go to completion (i.e. the reaction is slower at lower temperatures).

The hydrocarbonaceous feedstock is typically suspended above the bottom of the reactor vessel, such as by a metal support, and heated for a suitable amount of time, such as a time ranging from and including about five (5) minutes to one hundred and eighty (180) minutes. Embodiments of methods for producing a solid biofuel from hydrocarbonaceous feedstock further includes the step of maintaining the reactor vessel at a suitable pressure, ranging from and including about 50 psi to 800 psi. In theory, pressure and temperature are not independent variables. In other words, the temperature required for the reaction process will likely determine the pressure, and vice versa. For example, once the temperature is set, the desired pressure will typically also be known for the reaction process. However, there are confounding variables as none of the gasses act as ideal gasses so the calculated pressure will be somewhat different than the theory suggests. For example, pressure is the sum of the vapor pressures of each component, such as volatile chemicals, catalyst, water, carbon dioxide formed in the reaction, etc. For the reaction process, at a temperature of 170° C. the pressure will likely be 115 psi (7.9 bar or 0.79 MPa), while at a temperature of 270° C. the pressure will likely be 800 psi (55 bar or 5.5 MPa), for example. It is important to control the temperature and monitor the pressure to protect the reactor vessel from over-pressurizing. If, for example, the temperature exceeds 260° C. decarboxylation reactions become significant, since these reactions are exothermic and involve $CO_2$ gas so the reactor vessel can be damaged by a runaway decarboxylation reaction. Therefore, for most applications, the process temperature is desirably at or below 250° C., for example.

In embodiments, it is desirable that the catalyst used is a suitable acid, such as an organic acid, including but not limited to acetic, carbonic, formic, maleic, oxalic acids and combinations thereof, wherein the organic acid has an acidity ranging from about 1.5 pKa to 5.0 pKa. In embodiments, the acid may include an inorganic acid, such as sulphuric, hydrochloric, hydrobromic, nitric and phosphoric acids and combinations thereof. Embodiments of methods for producing a solid biofuel from hydrocarbonaceous feedstock can further include the step of drying the polymeric biofuel overnight.

In an embodiment, the hydrocarbonaceous feedstock is wet with a moisture content greater than 20%, desirably 50%. It is to be noted that the hydrocarbonaceous feedstock may be selected from the group consisting of woodchips, sawdust, softwood, hardwood, decadent hemlock, beetle-killed pine, bark, forest cuttings, branches, leaves, birch, alder, balsam, cedar, pulp, paper, cardboard, plant biomass (including: water hyacinths, milfoil, algae, and including but not limited to, marine plants, algae, cyanobacteria), agricultural waste, greenhouse cuttings, straw, corn stover, food processing wastes, fruit and vegetable waste, animal waste, horse manure, cow manure, pig manure, municipal wastes, food waste, yard waste, coffee grounds, waste cardboard and waste paper or a combination thereof. Further, embodiments of methods for producing a solid biofuel from hydrocarbonaceous feedstock may also result in polymeric biofuel having a yield that is at least 20%. The yield is the ratio of the moles of the product, such as the biofuel, over the moles of the reactants, such as the feedstock.

In other embodiments, methods for producing valuable organic chemicals from hydrocarbonaceous feedstock include the steps of loading a hydrocarbonaceous feedstock into a reactor vessel, introducing saturated steam including a catalyst into the reactor vessel, heating the reactor vessel to a suitable temperature, such as to a temperature of at least 170° C., to catalyze the reaction of hydrocarbonaceous feedstock under saturated steam conditions for a time sufficient to yield polymeric biofuel, isolating the liquid containing valuable organic chemicals from the reactor vessel, wherein the valuable organic chemicals are selected from the group consisting of furfural, 2,5 hydroxymethyl furfuraldehyde, acetic acid, formic acid, and levulinic acid.

Embodiments of apparatuses for producing biofuel include at least one reactor vessel, a basket, such as a removable basket, for holding the hydrocarbonaceous material, the basket being positioned in the reactor vessel and supported on a metal support above the bottom of the reactor vessel, wherein a space between a catalyst solution and the basket in the reactor vessel is configured to be filled with a catalyzed saturated steam, a heating element, such as a heater, positioned beneath the reactor vessel, the heating element being configured to heat the reactor vessel to a suitable temperature, a cover, such as a lid cover, removably positioned on the reactor vessel, the cover being configured for enabling inputting hydrocarbonaceous feedstock and outputting biofuel from the reaction vessel. It is to be noted that in embodiments of the apparatuses for producing biofuel the apparatuses may also include a plurality of reaction vessels in communication with each other.

In embodiments, the heating element for the apparatuses for producing biofuel may also include a boiler chamber positioned in communication with the at least one reactor vessel and configured to supply steam and a catalyst into the reactor vessel. Embodiments of apparatuses for producing biofuel may also include a chamber positioned in communication with the at least one reactor vessel for receiving the biofuel or other reaction product from the at least one reactor vessel. The chamber may include a condenser and a discharge port for discharging the biofuel. Embodiments of apparatuses for producing biofuel may further include a container positioned in communication with the chamber, the container being configured to collect the biofuel discharged from the chamber.

As used herein, the term "biomass" is given its conventional meaning in the art and is used to refer to any organic source of energy or chemicals that is renewable. Generally, the term "biomass" as used herein, refers to organic matter harvested or collected from a renewable biological resource as a source of energy. The renewable biological resource can include plant materials, animal materials, and/or materials produced biologically. The term "biomass" is not considered to include fossil fuels, which are not renewable.

The term "biofuel" as used herein, refers to any renewable solid, liquid or gaseous fuel produced biologically and/or chemically, for example, those derived from biomass. Most biofuels are originally derived from biological processes such as the photosynthesis process and can therefore be considered a solar or a chemical energy source. Other biofuels, such as natural polymers (e.g., chitin or certain sources of microbial cellulose), are not synthesized during photosynthesis, but can nonetheless be considered a biofuel because they are biodegradable. There are generally considered to be three types of biofuels derived from biomass synthesized during photosynthesis, namely, agricultural biofuels (defined below), municipal waste biofuels (residential and light commercial garbage or refuse, with most of the recyclable materials such as glass and metal removed) and forestry biofuels (e.g., trees, waste or byproduct streams from wood products, wood fiber, pulp and paper industries). Biofuels produced from biomass not synthesized during photosynthesis include, but are not limited to, those derived from chitin, which is a chemically modified form of cellulose known as an N-acetylglucosamine polymer. Chitin is a significant component of the waste produced by the aquaculture industry because it comprises the shells of seafood.

The term "moisture content" as used herein, refers to percent moisture of biomass. The moisture content is calculated as grams of contained liquid, such as water, per gram of wet biomass (or mass of wet biomass minus the mass of dry biomass all divided by the mass of wet biomass). As such, when used without qualification herein, the % moisture content refers to a total weight basis.

The term, "hydrocarbonaceous feedstock" is given its conventional meaning to refer to solid biomass such as wood or wet wood including other polysaccharides, cellulose, hemicellulose, lignin, a sugar, wood chips cellulose that ultimately contain hydrocarbons to produce polymeric biofuel. Embodiments of methods of the present invention involves placing the hydrocarbonaceous feedstock into the reaction vessel that can be sealed and pressurized, then heating the reaction vessel, and introducing a steam entrained volatile catalyst for a suitable time, and a suitable temperature as is necessary to convert the feedstock into a biofuel. There are various volatile chemicals that will work as a catalyst and examples of these volatile chemicals have been enumerated herein. The composition of and the amount of each chemical in the steam entrained volatile catalyst is dependent on the chemical's vapor pressure. The higher the temperature the more catalyst will be entrained in the steam. The hydrocarbonaceous feedstock can include the following: wood, woodchips, sawdust, softwood, hardwood, decadent hemlock, beetle-killed pine, bark, forest cuttings, branches, leaves, birch, alder, balsam, cedar, pulp, paper, cardboard, plant biomass (including: water hyacinths, milfoil, algae, and including but not limited to, marine plants, algae, cyanobacteria), agricultural waste, greenhouse cuttings, straw, corn stover, food processing wastes, fruit and vegetable waste, animal waste, horse manure, cow manure, pig manure, municipal wastes, food waste, yard waste, coffee grounds, waste cardboard and waste paper.

The term "valuable organic chemicals" as defined herein refers to volatile chemicals in solution, that may include chemicals such as furfural, 2,5 hydroxymethyl furfuraldehyde, acetic acid, formic acid, and levulinic acid but not limited thereto.

As used herein, the term "volatile acid" is defined as those acids that can be converted into a gaseous form. For example, the volatile acid may be one or more volatile weak acid having a pKa below 5.0. In a specific embodiment the weak acid may be one or more of phosphoric acid, or a carboxylic acid such as formic acid, acetic acid, maleic acid or maleic anhydride. In other instances, the volatile acid may be one or more volatile strong acids such as: hydrochloric acid, nitric acid or sulfuric acid or a mixture of these acids. Examples of the pKa and the boiling point of the volatile acids are provided in Table 1.

TABLE 1

| Volatile Weak Acid | pKa | Boiling Point ° C. |
|---|---|---|
| Formic Acid, HCOOH | 3.745 | 100.8 |
| Acetic Acid, $CH_3COOH$ | 4.756 | 118-119 |
| Maleic Acid, $C_4O_4H_4$ | 1.90 | 202 |
| Phosphoric Acid $H_3PO_4$ | 2.16 | 158 |

The feedstock is treated on a batch basis. The feedstock is sealed in the reactor vessel and heated to a suitable processing temperature, and then heated compressed saturated steam containing the volatile catalyst is introduced into the reactor vessel allowing the steam/volatile catalyst to condense on the feedstock and be absorbed into the feedstock to catalyze the conversion of the feedstock to a biofuel. The temperature dependence of the rate of reaction is described by the Arrhenius equation that says the rate the reaction is dependent on the rate constant for the reaction. The rate constant is given by:

$$k = Ae\frac{-Ea}{RT}, \text{ or } k = A\exp(-Ea/(RT))$$

where Ea is the activation energy and R is the gas constant. At higher temperatures the rate of the reaction increases. In practice, experimentation is typically used to determine the reaction parameters for a particular feedstock/catalyst combination, for example.

The reactor vessel is then maintained at the processing temperature and pressure for such time that the feedstock is converted to a biofuel. The temperature is maintained using a temperature controller, such as a thermostat, thermocouple and controller to control the heater to turn on the heater when the temperature in the boiler or reactor falls, for example. The temperature is changed in the reactor vessel by varying the power going to the heater. The saturated steam pressure is dependent upon the temperature and this pressure is monitored, such as by reading the pressure gauge from or associated with the reactor vessel. The process of heating the reactor vessel, could be automated with a manual override built into the reaction process to control the reaction temperature for the reaction process.

In embodiments, after the processing time for the reaction process has been completed, the reactor vessel will be allowed to cool naturally to room temperature before opening the reactor vessel to remove the biofuel. The reactor vessel is held at the processing temperature for a sufficient time as to allow the reaction of the feedstock to be formed into a biofuel, as can depend on the biofuel and amount of the biofuel being produced, for example. In other embodiments, after the processing time is completed, a valve on the reactor vessel will be opened allowing the hot compressed steam and volatile and valuable chemicals, such as organic chemicals, to be transferred to a blowdown tank. The pressure release will cool the biofuel reactor vessel through the evaporation of any residual liquids in the reactor vessel and the biofuel, thereby drying the biofuel. The blowdown tank may be cooled allowing the steam and volatile chemicals to condense in the blowdown tank. The water and volatile chemicals can then be recovered from the blowdown tank.

The blowdown tank may be connected to the atmosphere through a condenser that allows the condensation and collection of the volatile chemicals from the vapor phase. In other words, the blowdown tank typically should not be open to the atmosphere rather, a condenser is desirably used to collect any volatiles that may escape into the atmosphere. In some embodiments the reactor vessel will be heated by steam without a catalyst. In such case, the steam will condense on the feedstock at an elevated temperature and pressure and a volatile catalyst of formic and acetic acid will form endogenously in the biomass to facilitate the conversion of the feedstock to a biofuel.

In another embodiment, the feedstock will be loaded into a basket that is removably positioned inside the reactor vessel. The basket facilitates the loading of feedstock and the unloading of solid biofuel. In other embodiments wherein the feedstock is directly placed into the reactor vessel, such as without a basket, the solid biofuel is removed through vacuum suction. In some embodiments the reactor vessel may include a valve positioned at the bottom of the reactor vessel that is of a sufficient size to allow the solid biofuel to be removed from the reactor vessel once the valve is opened. The pressure in the reactor vessel is desirably controlled by a relief valve, and the pressure in the reactor vessel can be released and the basket holding the reaction product biofuel can be removed. If a basket is not used to hold the feedstock, the reactor vessel, in other embodiments, can have a large valve at the bottom of the reactor vessel that can be opened to allow the biofuel to fall out of the reactor vessel once the reactor vessel has cooled to below the boiling point of water, as the reactor vessel desirably should not be opened or the biofuel or reaction product removed, such as where the reactor vessel is at the operating pressure for the reaction process, for example.

In embodiments, the processing temperature can be any suitable temperature, such as desirably in a range of from and including 170° C. to 300° C., for example, or at other suitable reaction temperatures or reaction temperature ranges where the reaction will occur at a reasonable rate or an economic rate. The processing pressure in the reaction vessel may be any suitable pressure, such as a pressure of at least 0.8 MPa, which is not to be construed in a limiting sense. It is to be noted that the biofuel produced may have a heating value of at least 23 MJ/kg.

The drying of the biofuel is performed so as to have a suitable moisture content, such as a moisture content of less than 15%, as may be facilitated by the hydrophobic nature of the biofuel and may be achieved by a rapid reduction of pressure at operating temperature which is facilitated through the opening of a valve to allow a pressure release into a blowdown tank, for example.

The liquids, or effluent, recovered from the blowdown tank can be mixed with the incoming feedstock prior to the feedstock being placed into the reactor vessel. In exemplary embodiments, some of the carboxylic acids and volatile components that are recycled may be incorporated into the biofuel. Due to the acidic nature of the liquids from the blowdown tank, when recycled and mixed with the incoming feedstock, these chemicals will assist in catalyzing the reaction converting the feedstock to a biofuel. Also the liquids, or effluent, recovered from the reaction process can be recycled or re-used for use in future processing of the feedstock into biofuel or for producing valuable organic chemicals from the feedstock, such as hydrocarbonaceous feedstock, for example, in that the effluent recovered from the blowdown tank or from the reactor vessel(s) can include the catalyst or as can provide, through the reaction process, a catalyst, can be saved and re-used, or recycled, for future processing of the feedstock into biofuel or for producing valuable organic chemicals from the feedstock, for example. Another aspect of the invention provides embodiments of methods for the extraction of volatile chemicals in the plant-based feedstock. In such embodiments of methods, the feedstock that contains volatile chemicals that are of interest is placed in the reactor vessel and the reactor vessel is sealed and then heated to the operating temperature either by the injection of saturated steam, with or without catalyst, or by heating the reaction vessel and then injecting saturated steam with the volatile catalyst for the appropriate processing time. If the reactor vessel is not sealed during the reaction process, the temperature will not increase above 100° C. as the water in the reactor vessel will simply boil off. If the reactor vessel boils dry, the temperature can increase potentially damaging the reactor pressure seals and ruining the feedstock. Accordingly, the reactor vessel desirably needs to be sealed during the reaction process to keep the water inside the reactor vessel so as to maintain the liquid water below and saturated steam above the water in the reactor vessel. The valve between the reactor vessel and the blowdown tank is opened allowing the pressure to equalize causing the volatile chemicals to be transferred to the blowdown tank. Since the blowdown tank is cooler than the reactor vessel, the steam and volatile chemicals will condense in the blowdown tank where they can be collected. The volatiles and steam in the reactor vessel are under pressure when the valve is opened between the reactor vessel and the blowdown tank and the saturated steam and entrained volatiles flow into the blowdown tank where they cool and condense. The reactor vessel is desirably isolated from the boiler system, and the valve to the blowdown tank is opened allowing a rapid depressurization and evaporative cooling of the reactor vessel. Once the reactor vessel is at atmospheric pressure, the vessel may be opened and the feedstock removed.

It should be noted that embodiments of apparatuses and methods desirably can provide for extracting and collecting volatile chemicals already present in the feedstock. In the wood processing literature, these chemicals are noted as extractives and are usually harvested via solvent extraction.

In embodiments, a cooled condenser may be included between the blowdown tank and the atmosphere desirably allowing lower temperature volatiles to be collected.

Embodiments of invention provide for a methods for producing valuable organic chemicals such as carboxylic acids such acetic, formic and levulinic acids and HMF and furfural. These are carboxylic acids and fural derivatives that are formed during the acid catalyzed dehydration of cellulose and hemicellulose contained in biomass such as woody plant materials. In some embodiments the biomass is heated in a batch sealed in the reactor vessel by saturated steam containing one or more volatile catalysts. During the heating process, water and the volatile catalyst will condense onto the biomass catalyzing the production of the volatile chemicals. The extraction of the volatile chemicals is achieved by opening the reactor vessel valve to the blowdown tank, which is at room temperature and pressure. The saturated steam and volatile chemicals will be transported to the blowdown tank where the chemicals will condense so that a water solution containing the chemicals can be recovered.

Further aspects of the invention and specific example embodiments of the invention are described below and/or illustrated by the accompanying drawings.

Referring now to FIG. 1, there is illustrated an embodiment of a catalyzed steam biofuel reactor 100 for biofuel production according to the teachings of the present invention. FIG. 1 represents a batch plant where a single reactor vessel contains the catalyst solution, the feedstock and a method of heating the reactor vessel. The reactor vessel is a pressure vessel that typically needs to operate at around 240° C. and 3.5 MPa containing an acidic solution, for example. The reactor vessel may be made from any suitable type of strong, chemically resistant material, such as stainless steel, or other suitable material, and should not be construed in a limiting sense. The piping and valves may also be made from any type of strong, chemically resistant material, such as stainless steel, because stainless steel typically would work well for the organic weak acid catalysts. The biofuel reactor 100 includes a reactor vessel 102, such as a reactor pressure vessel, that includes a removable basket 104 for placing therein a hydrocarbonaceous feedstock 108, as well as for lifting the feedstock 108, and the produced biofuel from the feedstock 108 out of the pressure vessel 102. The removable basket 104 may be supported on a support 106 that can be made of metal. The reactor vessel 102 further includes a heating element 112, such as a heater 112, positioned at the bottom of the reactor vessel 102 and a catalyst solution 110. Preferably, the hydrocarbonaceous feedstock 108 is suspended above the catalyst solution 110, such as in the removable basket 104 so that the hydrocarbonaceous feedstock 108 is not in direct contact with the catalyst solution 110. Between the catalyst solution 110 and the basket 104 is saturated steam in air, for example, for the reaction process. The reactor vessel 102 includes a lid 114, such as a removable lid positioned on the top of the reactor vessel 102 for enclosing the reactor vessel 102 as well as for admitting the hydrocarbonaceous feedstock 108 and for removing the produced biofuel.

To admit the feedstock 108, the lid 114, or other suitable closure mechanism, or a valve, would be opened when the reactor vessel 102 is at atmospheric pressure and the feedstock 108 is then dumped or otherwise suitably added into the reactor vessel 102. The process of filling feedstock 108 into the reactor vessel 102 can include, for example, manually dumping the feedstock 108 into the open reactor vessel 102, or the feedstock 108 could be conveyed to the reactor vessel 102 and dumped into the reactor vessel 102, such as using a conveyer belt that dumps the feedstock 108 into the reactor vessel 102. The valve, lid 114, or other suitable closure mechanism, would then be closed and sealed prior to heating and admitting steam to the reactor vessel 102 for the reaction process. The lid 114 could be removed manually, or a servo motor could be employed to remove the lid 114. The lid 114 can be a 'knife-gate valve' with an actuator that opens and closes it remotely, for example, but an automated operation of the lid 114 is desirable to a manual operation of the lid 114. In various operations, it is more desirable that the lid operation would be done automatically, rather than manually. Various suitable reactor vessels 102 can be used and various suitable lids 114, as known in the art, and can be fastened or joined to each other by various suitable methods so to open and close the reactor vessel 102. For example, a blind flange could be bolted to the top of the reactor vessel 102 to form a lid 114. In such case, it could be done by unbolting and lifting the lid 114 15 manually. Also, a motorized winch could be used to lift the flange as it typically could weigh several hundred pounds, for example. Another method would be to use a gate valve as the lid 114. In such case, the valve would be opened to admit the feedstock 108 and closed to allow the reactor vessel 102 to be pressurized. The valve could be controlled manually or automatically depending on the level of automation required. Pressure vessel lids, closures and large valves are known in the art and in the pressure vessel manufacturing process, as can be suitable for use in the biofuel reactor 100.

Once the reactor vessel 102 is at atmospheric pressure the reactor vessel 102 may be opened by opening the lid 114 and the biofuel made from the feedstock 108 removed manually. Once the reactor vessel 102 has cooled and the pressure in the reactor vessel 102 is released, the lid 114 can be opened and the biofuel removed from the reactor vessel 102, such as by removing the basket 104 or by sucking the processed material, such as the biofuel or reaction product, out of the reaction vessel 102 with a vacuum suction device, such as a large commercial shop vacuum, or other suitable suction device, for example. When a plurality of reactor vessels 102 are used, the reactor vessels 102 are desirably designed to be replicas of or similar to each other so that typically the same amount of feedstock 108 and the same amount of catalyzed steam would be added into the reactor vessel 102. The reaction process in the reactor vessel 102 can be controlled by monitoring the temperature and pressure and suitably adjusting the amount of steam used in the reaction process, for example. The pressure in the reactor vessel 102 is measured using a pressure gage 118 attached to the reactor vessel 102 positioned over the lid 114. The reactor vessel 102 also desirably has a pressure relief safety valve 124 and/or a rupture disk 124 to protect the reactor vessel 102 from exceeding the maximum amount of pressure that the reactor vessel 102 can withstand. The standards for pressure in North America are the ASME pressure vessel standard. The temperature in the reactor vessel 102 is measured via a thermocouple 122 that protrudes into the reactor vessel 102. The reactor vessel 102 can further include an outlet port 116 located at the bottom of the reactor vessel 102 that can be used to drain the catalyst solution 110 out of the reactor vessel 102. Also the liquids, or effluent, recovered from the reaction process can be recycled or re-used for use in future processing of the feedstock into biofuel or for producing valuable organic chemicals from the feedstock, such as hydrocarbonaceous feedstock, for example, in that the effluent recovered from the reactor vessel 102, such as from the outlet port 116, can include the catalyst or as can provide, through the reaction process, a catalyst, as can be saved and re-used, or recycled, for future processing of the feedstock into biofuel or for producing valuable organic chemicals from the feedstock, for example. The pressure and temperature in the reactor vessel 102 can be maintained manually or by an automated control, desirably the maintenance of the pressure and temperature is by automated control with the ability to manually override the automated control, as necessary or desirable. The temperature in the reactor vessel 102 for the reaction process can desirably be monitored and controlled by varying the power going to a heater, such as to a heater 112, such as can be positioned beneath the reactor vessel 102, that provides heat to the reactor vessel 102, accordingly. The pressure in the reactor vessel 102 for the reaction process typically depends on the temperature, but the pressure is primarily monitored for safety concerns in and during the reaction process in the reactor vessel 102.

Figure 2:
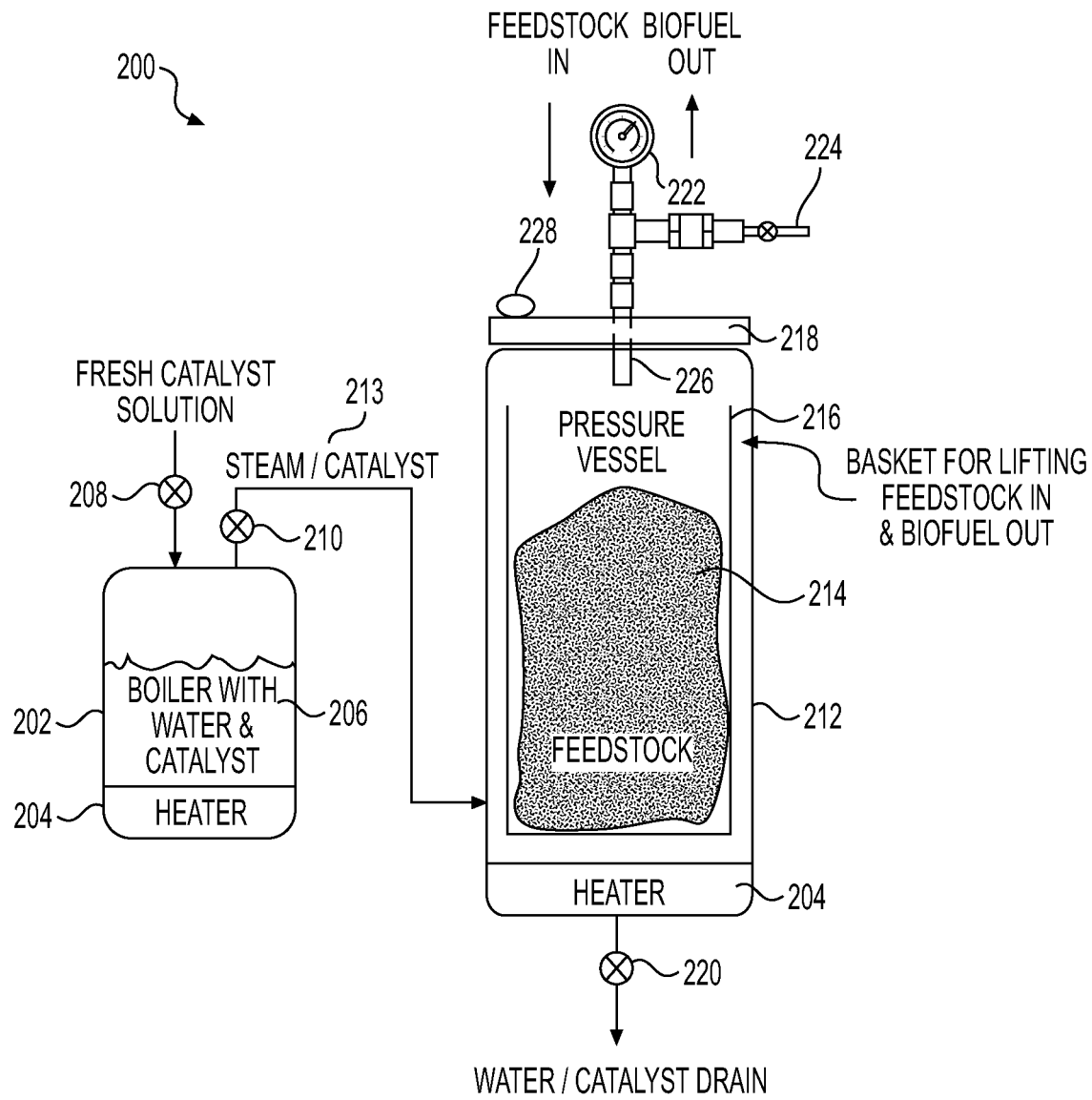
FIG. 2 is a side sectional view of an embodiment of the reactor vessel showing the boiler chamber in communication with the reaction vessel, according to the present invention.

FIG. 2 illustrates another embodiment of a catalyzed steam biofuel reactor 200 for biofuel production constructed according to the teachings of the present invention. FIG. 2 is a schematic diagram illustrating a batch plant for the production of a solid biofuels where the saturated steam and volatile catalyst is produced in a separate boiler system and is introduced into the reactor/pressure vessel by opening a valve connecting the two systems. Heating the catalyst solution will produce a steam containing the volatile catalyst. The condensation of the steam/catalyst solution will heat the feedstock and, in turn, transport the catalyst to the feedstock. An enclosed boiler chamber 202 for generating steam includes a heating element 204 for heating the water and catalyst mixture 206. The volatile catalyst or catalysts are dissolved in water making a dilute solution of the catalyst in water. When heated, the water undergoes a phase change to a gas as do the volatile catalysts. This makes the catalyzed saturated steam that is used in the reaction process. Both the boiler chamber 202 and the biofuel reactor 200 are desirably made of stainless steel, or other suitable material, for example, as can depend on the biofuel produced, the process or application, and should not be construed in a limiting sense. The boiler chamber 202 may be made from any suitable corrosion resistant material, such as stainless steel, that can withstand temperatures typically of up to 250° C., and pressure up to 5 MPa, and an acidic environment, or can withstand other suitable temperatures and pressures and can depend on the biofuel produced, the process or application, and should not be construed in a limiting sense.

The boiler chamber 202 includes an inlet port 208 and an outlet port 210 for directing the steam that is generated in the boiler chamber 202 to a biofuel reactor vessel 212 similar to that described in FIG. 1, which corresponds to reactor vessel 102. The reactor vessel 10 212 receives the mixture of a steam/catalyst 213 from the boiler chamber 202 for undergoing hydrothermalization of a hydrocarbonaceous material or feedstock 214 suspended in a basket 216. The reactor vessel 212 includes a lid 218, such as a removable lid, positioned on top of the reactor vessel 212 for enclosing the reactor vessel 212. The lid 218 may be removed to open the reactor vessel 212 such that the hydrocarbonaceous feedstock 214 may be inserted into the reactor vessel 212 and so that the produced biofuel or reaction product can be removed from the reactor vessel 212. For example, to insert the feedstock 214 into the reactor vessel 212, the lid 218, closure or valve may be opened when the reactor vessel 212 is at atmospheric pressure and the feedstock 214 is then dumped or placed into the reactor vessel 212. The process of filling the feedstock 214 into the reactor vessel 212 is known in the art. For example, the feedstock 214 20 could be manually dumped into the open reactor vessel 212, or it could be conveyed to the reactor vessel 212 and dumped in using a conveyer belt that dumps the feedstock 214 into the reactor vessel 212. The valve, lid 218 or closure would then be closed and sealed prior to heating and admitting steam to the reactor vessel 212 for the reaction process. The pressure in the reactor vessel 212 is measured using a pressure gage 222 attached to the reactor vessel 212 positioned over the lid 218. The reactor vessel 212 desirably has a pressure relief safety valve 228 and/or a rupture disk 228 to protect the reaction vessel 212 from exploding. The pressure standards in North America are the ASME pressure vessel standard. The temperature in the reactor vessel 212 is measured via a thermocouple 226 that protrudes into the reactor vessel 212. The reactor vessel 212 can further include an outlet port 220 at the bottom of the reactor vessel 212 that can be used to drain the water and catalyst solution out of the reactor vessel 212. Also the liquids, or effluent, recovered from the reaction process can be recycled or re-used for use in future processing of the feedstock into biofuel or for producing valuable organic chemicals from the feedstock, such as hydrocarbonaceous feedstock, for example, in that the effluent recovered from the reactor vessel 212, such as from the outlet port 220, can include the catalyst or as can provide, through the reaction process, a catalyst, as can be saved and re-used, or recycled, for future processing of the feedstock into biofuel or for producing valuable organic chemicals from the feedstock, for example. The steps in the reaction process can be summarized as follows. First, the reactor vessel 212 is empty and open to the atmosphere at the start. The reactor vessel 212 is filled with feedstock 214 and sealed. The reactor vessel 212 is heated to the operating temperature by means of a heater 204 or by the admission of catalyzed steam from the boiler chamber 202 or both. The reactor vessel 212 is held at the processing temperature for a suitable time so as to allow the reaction of the feedstock 214 to form therefrom a biofuel or reaction product. The reactor vessel 212 is isolated from the boiler chamber 202 or boiler system 202 and the valve to a blowdown tank is opened allowing a rapid depressurization and evaporative cooling of the reactor vessel 212. Once the reactor vessel 212 is at atmospheric pressure the reactor vessel 212 may be opened and the feedstock 214 or the formed biofuel or reaction product removed from the reactor vessel 212. After the biofuel is removed from the reactor vessel 212, the reaction process can start all over again for the biofuel or reaction product production in the reactor vessel 212.

Figure 3:
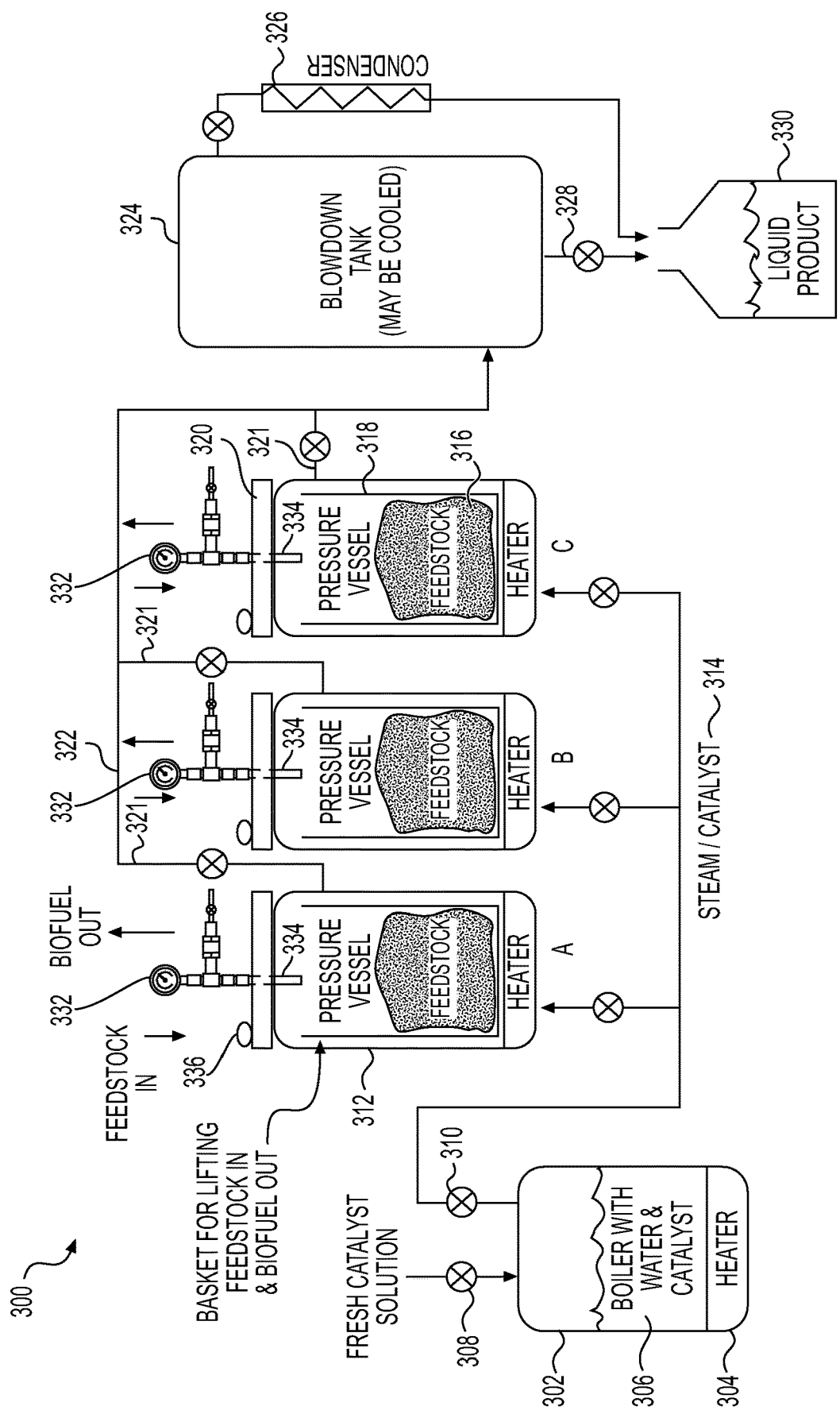
FIG. 3 is a side section view of an embodiment showing a plurality of the reactor vessels in communication with each other and with a boiler chamber, a blowdown chamber and a collection vessel for reaction product, according to the present invention.

FIG. 3 further depicts another embodiment of an exemplary catalyzed steam biofuel reactor 300 for biofuel production constructed according to the teachings of the present invention. FIG. 3 illustrates a multiple reactor plant for the production of solid biofuel and a solution of volatile chemicals in water. The system of the biofuel reactor 300 uses a separate boiler system to generate the steam/volatile catalyst and a blowdown tank with a condenser to recover the volatile chemicals from the steam released from the reactor vessel. In the biofuel reactor 300, an enclosed boiler chamber 302 for generating steam includes a heating element or heater 304 for heating water or a water and catalyst mixture 306 in the boiler chamber 302. As discussed herein, the volatile catalyst or catalysts are dissolved in water making a solution of the catalyst in water. When heated, the water undergoes a phase change to a gas as do the volatile catalysts. This makes the steam or the catalyzed saturated steam that is used in the reaction process. The boiler chamber 302 includes an inlet port 308 for admitting water or a fresh catalyst solution and an outlet port 310 configured for directing the steam generated in the boiler chamber 302 to a plurality of the biofuel reactor vessels 312, similar to the reactor vessel 102 as described in FIG. 1, which corresponds to the reactor vessels 312. As in the other embodiments described herein, piping 322 and valves associated with reactor vessels 312 and the biofuel reactor 300 are also made from a suitable material, such as stainless steel, for example, or other suitable material, as can depend on the biofuel produced or the application, and should not be construed in a limiting sense. The reactor vessels 312 receive the mixture of a steam/catalyst 314 from the boiler chamber 302 for undergoing hydrothermalization of a hydrocarbonaceous material 316 or feedstock 316 suspended in a basket 318 in the corresponding reactor vessels 312. If the same type of feedstock 316 and the same amount of feedstock 316 is placed in the reactor vessels 312 then the same or substantially the same amount of steam/catalyst will be used for the reaction process. However, it is to be noted that inserting different feedstocks 316 in different reactor vessels 312 would likely impact the amount of steam/catalyst that would be used (i.e., that amount of steam/catalyst would likely be different) for the reaction process in the respective reactor vessels 312.

Each of the plurality of reactor vessels 312 includes a lid 320, such as a removable lid 320, positioned on top of the corresponding reactor vessel 312 for enclosing the corresponding reactor vessels 312, as well as for admitting the hydrocarbonaceous feedstock 316 and for removing the produced biofuel from the feedstock 316. The reactor vessels 312 are desirably designed to be replicas of or similar to each other so that the same amount of feedstock 316 and the same amount of catalyzed steam can be introduced into the reactor vessels 312. The reactor vessels 312 can be controlled by monitoring the temperature and pressure and adjusting the amount of steam used, such as either manually or by a suitable controller or processor, such as by a computer having the requisite programs for control of the biofuel reactor 300, for example. Typically, normally the same amount or substantially the same amount of feedstock 316 would go into each reactor vessel 312 assuming of course the same feedstock 312 and the same amount of feedstock 312 is used in each reactor vessel 312 in the biofuel reactor 300. Desirably, typically, normally the same type of feedstock 316 and the same amount of feedstock 316 would go into each reactor vessel 312 and then the same amount of the steam/catalyst 314 would be used in each reaction vessel 312 for the reaction process. However, in embodiments, different feedstocks 316 and/or different amounts of feedstock 316 could be placed in different reactor vessels 312, and then the amount of steam/catalyst 314 used in each reactor vessel 312 would likely be different from that used in the other reactor vessels 312, for example. An exemplary embodiment of the reactor process for the biofuel production typically can include the following. The reactor vessel 312 initially is empty and open to the atmosphere at the start. The reactor vessel 312 is filled with feedstock 316 and sealed. The reactor vessel 312 is then heated to the operating temperature desirably by means of a heater, as indicated in FIG. 3, associated with the corresponding reactor vessel 312 or by the admission of steam or catalyzed steam 314, or both. The reactor vessel 312 is held at the processing temperature for such time as to allow the reaction of the feedstock 316 with the steam/catalyst 314 to convert the feedstock 316 into a biofuel or reaction product. The reactor vessels 312 desirably are isolated from the boiler chamber 302 and a valve 321 to a blowdown tank 324 is opened allowing a rapid depressurization and evaporative cooling of the reactor vessels 312. Once the corresponding reactor vessel 312 is at atmospheric pressure, the reactor vessel 312 may be opened and the feedstock 316, which has been converted to biofuel or reaction product, removed from the corresponding reaction vessel 312. After the biofuel or reaction product is removed from the plurality of, one or more, reactor vessels 312 the reaction process can start all over again in the catalyzed steam biofuel reactor 300. While, three reactor vessels 312 are illustrated in FIG. 3, any suitable number of reactor vessels 312, and corresponding numbers of other components in the biofuel reactor 300, can be used, as can depend on the use, application, or the biofuel or biofuels or reaction products to be formed, and should not be construed in a limiting sense. In the reaction process, the reactor vessels 312 receive the mixture of the steam/catalyst 314 for undergoing hydrothermalization of the hydrocarbonaceous material 316 or feedstock 316 suspended in a corresponding basket 318 in a corresponding reactor vessel 312. The pressure is measured using a pressure gage 332 attached to each of the plurality of reactor vessels 312 positioned over the lid 320 of the corresponding reactor vessel 312. The reactor vessels 312 also have a pressure relief safety valve 336 and/or a rupture disk 336 to prevent each of the plurality of reactor vessels 312 from exploding. The temperature in each of the plurality of reactor vessels 312 is measured via a thermocouple 334 that protrudes into the corresponding reactor vessel 312. After completion of the catalyzed steam hydrothermalization process, the output steam and volatile organic chemicals from each of the reactor vessels 312, identified in FIG. 3 also as A, B and C, is admitted into the blowdown tank 324 for collection adapted with a condenser unit 326 configured to cool down the collected volatile organic chemicals or reaction product to room temperature. The blowdown tank 324 is typically made from a suitable material, such as stainless steel, or can be made or other suitable material, as can depend on the biofuel or reaction product or application, and should not be construed in a limiting sense. The blowdown tank 324 can further include an outlet port 328 at the bottom of the blowdown tank 324 adapted to drain the volatile organic chemical solution or reaction product out of the blowdown tank 324. The final volatile organic chemical product or liquid product is collected in a collection vessel 330 for later use. Also the liquids, or effluent, recovered from the reaction process can be recycled or re-used for use in future processing of the feedstock into biofuel or for producing valuable organic chemicals from the feedstock, for example, in that the effluent recovered from the blowdown tank 324, such as from the outlet port 328, can include the catalyst or as can provide, through the reaction process, a catalyst, as can be saved and re-used, or recycled, for future processing of the feedstock into biofuel or for producing valuable organic chemicals from the feedstock, for example. The plurality of the reactor vessels 312 desirably would be connected using stainless steel piping which is suitably sized correctly for the size of the reactor vessels 312 and the operating pressures and temperatures for the reaction process, or can be connected by other suitable connections or other suitable materials for forming the connections, as can depend on the biofuel or reaction product or application, for example, and should not be construed in a limiting sense. The connections between the reactor vessels 312 could also desirably include valves, such as either manual or automatically operated valves, to isolate and connect the reactor vessels 312, as needed, for example, for the reaction process. There could be a valve between the plurality of reactor vessels 312 and the boiler chamber 302, for example, such as could be closed to isolate the boiler chamber 302 from the rest of the biofuel system or biofuel reactor 300. Otherwise, the steam or the steam catalyst from the boiler chamber 302 could condense into the blowdown tank 324.

There are volatile organic compounds that are in the wood or feedstock and may be extracted by the acidic steam. These compounds depend on three factors: (1) being present in the feedstock; (2) being volatile; (3) and being stable at the processing temperatures. An example of these chemicals would be the processing of cedar feedstock. In this case, processing of cedar feedstock, such as by the methods and apparatuses of embodiments described herein, could be utilized to yield a number of valuable organic chemicals as volatile organic compounds including: β-thujaplicin, γ-thujaplicin, methyl thujate and thujic acid, for example. In particular, β-thujaplicin is quite valuable on the order of $5,000/Kg and comprises about 1% of the Western Red Cedar wood. To isolate the chemicals or volatile organic compounds from the solution, a person of skill in the art can use any known separation technique in the art, such as solvent extraction or preparative HPLC. For example, the extraction and purification of β-thujaplicin has been studied quite extensively in Japan for some time now, but Japan's variety of cedar is now in very short supply. The major problem of uptake of such volatile organic compounds or chemicals, such as β-thujaplicin, in industry is the relative lack of a reliable supply. Currently, it is believed that producing β-thujaplicin on a commercial scale is lacking, and having a reliable supply of β-thujaplicin would desirably allow cosmetic and skin care companies to formulate this chemical into their products.

Figure 4:
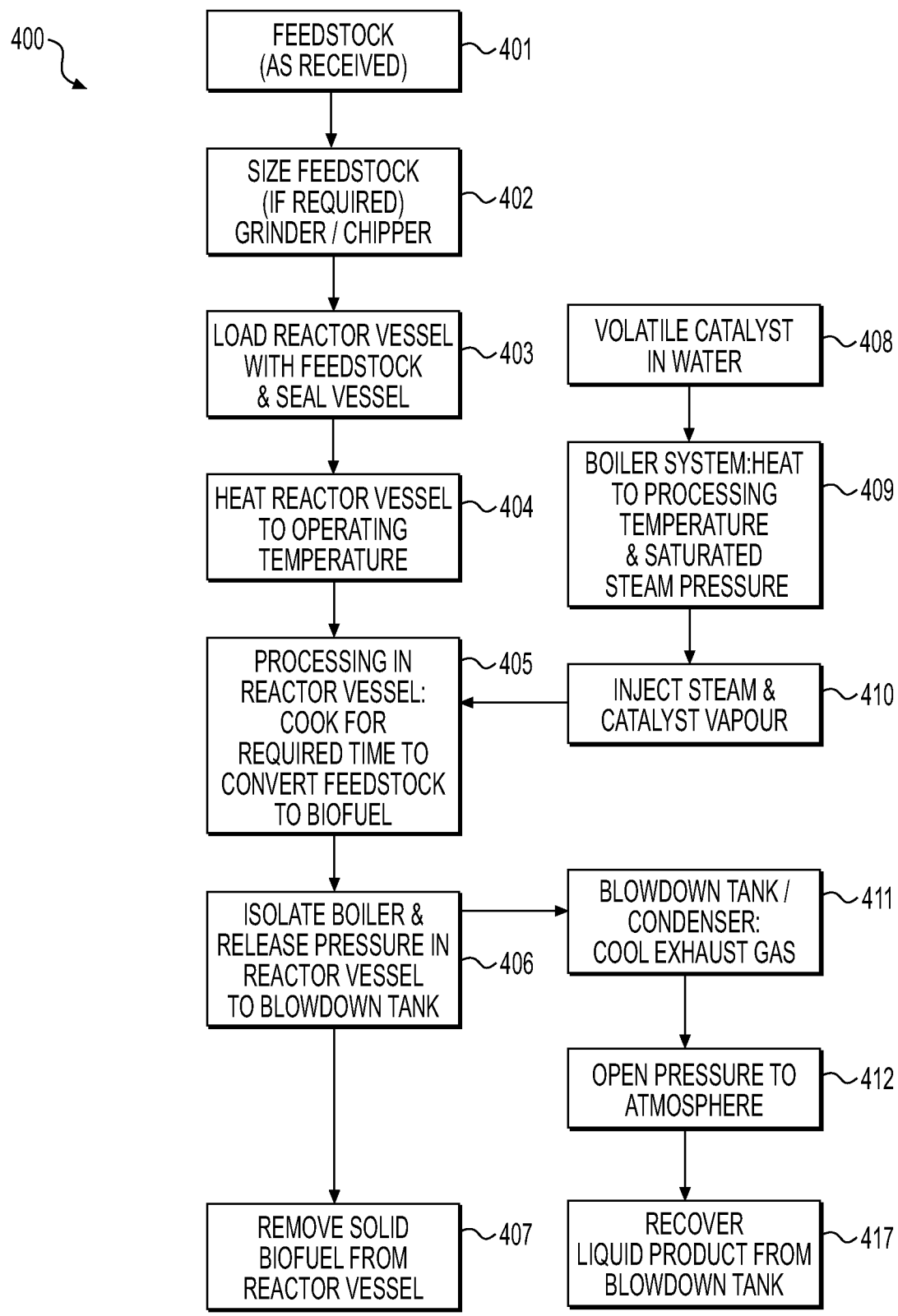
FIG. 4 is a representative block diagram process according to an embodiment of a process for producing biofuel, according to the present invention.

Referring now to FIG. 4, an embodiment of an exemplary process 400 for the production of biofuel and reaction product according to the embodiments of methods described herein is provided. Embodiments in the exemplary process including the steps of selecting the feedstock at step 401, which can be appropriately sized in a grinder or chipper at step 402 and loaded into the reactor vessel at step 403, which is subsequently sealed. It is to be noted that depending on the feedstock, the size of the feedstock can vary greatly. For example, forestry feedstocks can include everything from bark, branches, leaves, chips to whole logs. Typically, if there are larger feedstocks being utilized, a device called a wood hog could be used to grind up whole logs to small shredded chips of less than one inch, or other suitable size, for example. Other materials can be handled and prepared as feedstock and the industrial processes are or can be set to provide the appropriate sized material. For example, a large chipper can be used to reduce railroad tie sized logs to produce chips smaller than one (1) inch for the feedstock, for example. The feedstock can be loaded into the reactor vessel in any manner known to the person of ordinary skill in the art. In the next step 404, inside the reactor vessel, the feedstock is heated to the operating temperature. The heating of the feedstock may be done by turning the heater on and waiting for the appropriate temperature to be achieved. By utilizing steam from a boiler, the reaction process is much faster because the operating temperature can be achieved sooner, such as can be achieved in minutes, for example. The process is remarkably resilient to rates of temperature increase. A faster reaction process is better economically but a relatively slower reaction process can work equally as well, for example. The desired temperature for the reaction process is desirably in a range of from and including 210° C. to 240° C., as can depend on the feedstock and the catalyst type and composition, and should not be construed in a limiting sense. The processing time needs to be sufficient for the reaction process to go to completion and is typically in a range of from and including fifteen (15) minutes to one (1) hour, for example, as can depend on the use or application, and should not be construed in a limiting sense. Simultaneously, such as substantially simultaneously, a volatile catalyst in water at step 408 can be introduced into the boiler system at step 409 and brought to a desired processing temperature and saturated steam pressure. For example, the volatile catalyst in water is placed in the boiler and the boiler is heated to a suitable temperature, such as at or slightly above the desired processing temperature for the reaction process. The boiler is held at the desired temperature. The pressure is a consequence of heating the water above the atmospheric boiling point of water. The pressure is a fundamental property of the water at a particular temperature. The term saturated steam is used to denote that the pressure inside the reactor vessel is that expected for a closed system where the liquid (water) is in equilibrium with the gas phase (steam). There are standard tables to determine the pressure at a desired temperature. The pressure increases substantively with the temperature, which means that the pressure rating of the reactor vessel and its costs increase as well, so it is desirable to have the processing temperature as low as possible while still allowing the chemical reactions to occur in a timely manner. To admit the steam into the reactor vessel a valve is opened and, since the boiler or boiler chamber is at a higher pressure, the catalyzed saturated steam will flow into the reactor vessel. Since the feedstock is typically at a lower temperature than the steam, the steam or the steam and catalyst will condense on the feedstock and the reaction will occur to form the biofuel or reaction product. The desired processing temperature is in a range of from and including 210° C. and 240° C., depending on the feedstock, and should not be construed in a limiting sense. The saturated steam pressure desirably would be in a range of from and including 19 Bar (1.9 MPa) to 34 bar (3.4 MPa), for example, as can depend on the application, and should not be construed in a limiting sense.

The steam comprising the catalyst vapor at step 410 can be admitted, such as by injection, into the reactor vessel at step 405 and, at this point in the process, to catalyze the hydrothermalization process to convert feedstock into polymeric biofuel or reaction product. After the desired or suitable time, in the next step, the boiler or boiler chamber is isolated at step 406 and the pressure is released from the reactor vessel to the blowdown tank. For the pressure release, desirably there would be a valve between the plurality of reactor vessels and the boiler or boiler chamber of the boiler system. The boiler or boiler chamber of the boiler system is isolated by the valve which can be turned on when steam is required and turned off when steam is no longer required. This valve would be closed to isolate the boiler or boiler chamber from the rest of the biofuel system or biofuel reactor. Otherwise, the boiler steam would be condensing into the blowdown tank. Then, solid biofuel at step 407 can be removed manually from the reactor vessel. Once the reactor vessel is at atmospheric pressure the vessel may be opened and the biofuel or reaction product removed from the reactor vessel. The removal of the biofuel or reaction product from the reactor vessel or reactor vessels can be by any of various ways. Typically, the formed biofuel is in a basket and so the basket would be lifted out of the reactor vessel to remove the formed biofuel. Also, in embodiments, the feedstock is placed in the reactor vessel without a basket so the biofuel or reaction product can simply be vacuumed out of the reactor vessel, such as by using an industrial sized shop vacuum, or other suitable vacuum device or suitable suction device, for example. Also, in other embodiments, a large valve can be placed at the bottom of the reaction vessel which can be opened to remove the processed feedstock biofuel or reaction product. Meanwhile, the exhaust gas from the reactor vessel can be condensed in the blowdown tank at step 411 and the residual pressure can be released into the atmosphere at step 412. The reactor vessel is isolated from the boiler system or boiler chamber and the valve to the blowdown tank is opened allowing a rapid depressurization and evaporative cooling of the reactor vessel. Finally, the desired liquid product or a reaction product at step 417 from the blowdown tank can be recovered, such as by condensing the vapor and draining it into the container e.g., the collection vessel 330 such as for further use. As discussed with respect to the biofuel reactor 300 of FIG. 3, the liquid product or a reaction product formed from the reaction process in the reactor vessel can be removed when the valve between the reactor vessel and the blowdown tank is opened and the pressure differential moves the steam and volatile chemicals into the blowdown tank, for example. The more volatile components can be captured using a condenser that connects the blow down tank to the atmosphere, for example. Also, in the blowdown tank, the steam and volatile chemicals condense and form an aqueous solution in the bottom of the blowdown tank. To remove the solution of the processed product, a valve at the bottom of the blowdown tank can be opened to allow the liquid to drain into a recovery container or recovery flask, for example.

The following examples are provided to illustrate and compare the catalyzed steam hydrothermalization process of the exemplary embodiments described herein to convert feedstock/wood into biofuel, but should not be construed in a limiting sense.

Example 1

Process to Produce Biofuel from Red Alder Log

A red alder log was converted to shavings using a chain saw. The moisture content of the shavings of the red alder log was about 51.2% and the higher heating value (HHV) of the dried material was 17.92 MJ/kg. A wet 41.55-gram sample of the shavings (20.58 gm dry weight equivalent, [DWE]) of the biomass was placed in a container suspended in a 1 litre pressure vessel and 50 ml of 0.2 M of an aqueous maleic acid catalyst solution was placed in the bottom of the pressure vessel. The pressure vessel was sealed and heated to a temperature of about 230° C. and held at this temperature for thirty (30) minutes. After this time elapsed the pressure vessel was allowed to cool to room temperature. The biofuel was removed from the pressure vessel and dried overnight at 70° C. The yield of the biofuel was 11.2 grams or 54.35% based on dry weight equivalent of feedstock. The HHV of the biofuel was measured by bomb calorimetry to be 22.35 MJ/kg, which is an increase of 24.7% relative to the HHV of the initial dried shavings.

Example 2

Process to Produce Biofuel from Red Alder Log

The same feedstock that was used in Example 1 was used in Example 2: the moisture content of the shavings was 51.2% and the HHV of the dried material was 17.92 MJ/kg. A wet 36.38-gram (17.74 gram DWE) sample of red alder shavings was placed in a container suspended in a 1 litre pressure vessel and 25 ml of a 0.2 M maleic acid catalyst solution was placed in the bottom of the pressure vessel and the pressure vessel was sealed. The pressure vessel was heated to a temperature of about 230° C. and held at this temperature for thirty (30) minutes. The pressure vessel was then cooled to room temperature and the biofuel was removed. The biofuel was then dried in an oven at 70° C. overnight. The yield of the biofuel was 12.14 grams or 68.44% based on dry weight equivalent of feedstock. The HHV of the biofuel was measured by bomb calorimetry to be 22.10 MJ/kg, which is an increase of 23.3% relative to the HHV of the initial dried shavings.

Example 3

Process to Produce Biofuel from Red Alder Log

A red alder log was converted to shavings using a chain saw. The same feedstock that was used in Example 1 was also used in Example 3. The moisture content of the shavings was 51.2% and the HHV of the dried material was 17.92 MJ/kg. A wet sample of 41.0 grams (21.98 grams DWE) of the feedstock was placed in a container that was suspended in a pressure vessel. 50 ml of a 0.2 M maleic acid solution was placed in the bottom of the pressure vessel and the pressure vessel was sealed. The pressure vessel was heated to a temperature of about 230° C. and held at this temperature for thirty (30) minutes. The pressure vessel was then allowed to cool to room temperature before opening. The recovered biofuel was dried at 70° C. overnight. The amount of dry biofuel recovered was 12.35 grams which gave a yield of 56.19% based on dry weight equivalent of feedstock. The HHV of the biofuel was measured by bomb calorimetry to be 23.02 MJ/kg, which is an increase of 28.5%, relative to the HHV of the initial dried shavings.

Example 4

Process to Produce Biofuel from Wet Softwood Chips

An 82.10-gram (36.24 gram DWE) sample of wet softwood chips with a moisture content of 55.9% was placed in a container suspended in a pressure vessel. The HHV of the dried softwood chips was 18.10 MJ/kg. 50 ml of 0.2M maleic acid catalyst was placed in the bottom of the pressure vessel. The pressure vessel was sealed and heated to a temperature of about 230° C. and held at this temperature for one (1) hour. The pressure vessel was then allowed to cool naturally to room temperature. The biofuel was removed from the pressure vessel and dried in an oven at 70° C. overnight. The dry weight of the biofuel recovered was 19.64 grams giving a yield of 54.17%. The HHV of the recovered biofuel was measured by bomb calorimetry to be 25.73 MJ/kg, which is a 44% increase relative to the HHV of the initial dried softwood chips.

The proximate analysis was measured using a Mettler TGA/DSC1 using the ASTM E1131 Test Method for Compositional Analysis by Thermogravimetry. The results were corrected to zero moisture. The feedstock had 77.7% volatiles, 22.3% fixed carbon and 0% ash while the biofuel had 56.6% volatiles, 43.4% fixed carbon and 0% ash.

Figure 5:
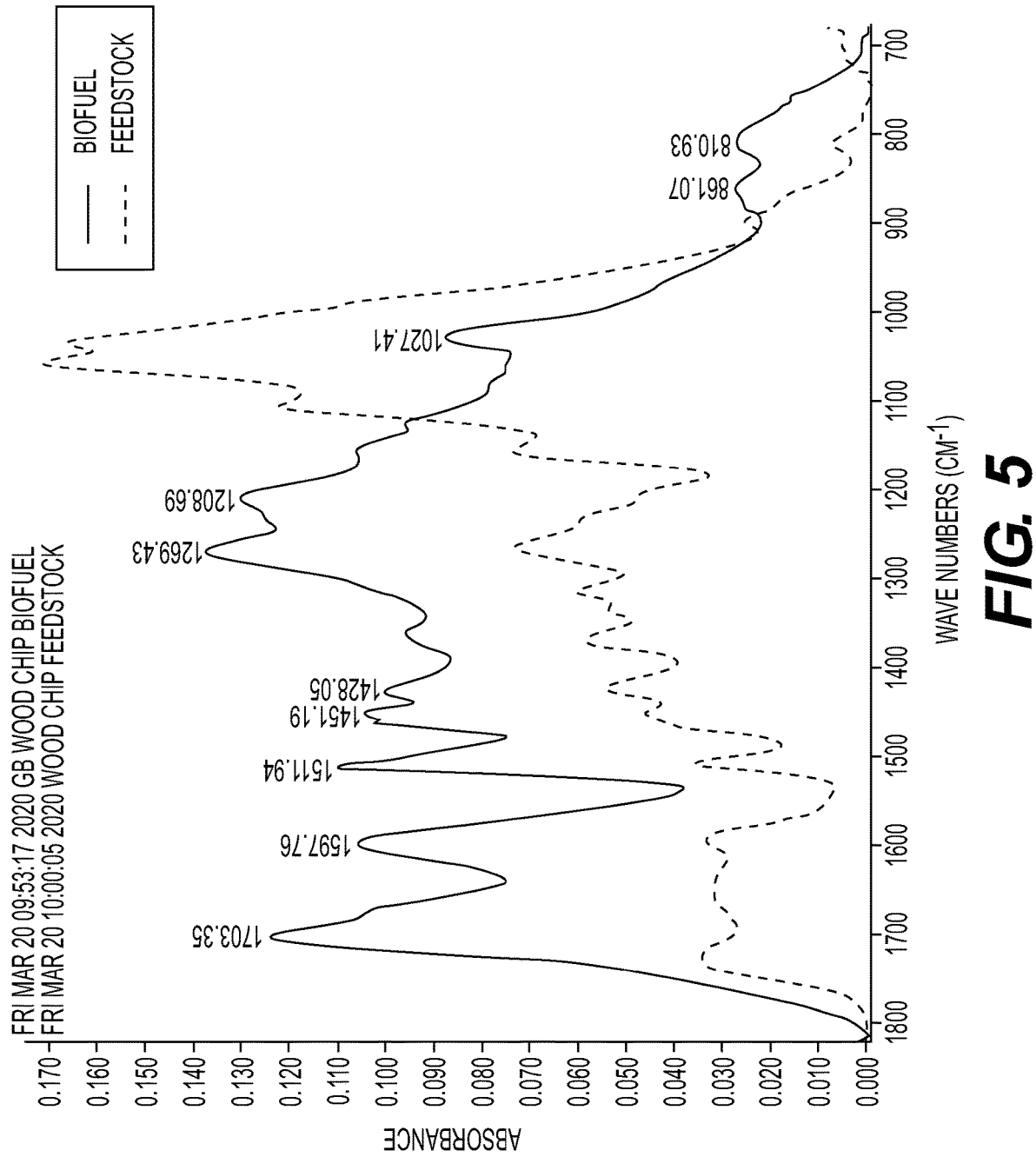
FIG. 5 is a representative FTIR spectrum from 1800 $cm^{-1}$ to 650 $cm^{-1}$ of the biofuel produced in Example 4, according to the present invention. The dashed line is the wood chip feedstock and the solid line is the biofuel produced in Example 4, according to the present invention.

FIG. 5 depicts the FTIR spectra from 1800 $cm^{-1}$ to 650 $cm^{-1}$ of the feedstock and the biofuel product. The dashed line shows the spectrum of the wood chip feedstock. The black line is the spectrum of the biofuel produced in Example 4. An interpretation of the infrared spectra of the biofuel is as follows: Peaks at 861 $cm^{-1}$ and 810 $cm^{-1}$ are due to C—H deformation out of plane, of aromatic rings. The biofuel peak at 1269 $cm^{-1}$ is due to an ether —O— symmetric stretch while the peak at 1208 $cm^{-1}$ is due to the asymmetric stretch. The peaks at 1451 $cm^{-1}$ and 1428 $cm^{-1}$ are due to C—H bending in the CH2 groups in the biofuel. The peak at 1597 $cm^{-1}$ is from aryl ring symmetric stretching. The peak at 1512 $cm^{-1}$ is due to aryl ring asymmetric stretching. The peak at 1703 $cm^{-1}$ is due to C═O stretch of unconjugated ketone, carbonyl and ester groups. The major peaks that are indicative of a biofuel are the C═O stretch of ketone, carbonyl and ester groups and the —O— symmetric and asymmetric stretch peaks at 1269 $cm^{-1}$ and 1208 $cm^{-1}$, respectively. In contrast to the biofuel, the FTIR spectrum of the wood chip feedstock is dominated by the peaks at 1056 $cm^{-1}$ and 1034 $cm^{-1}$. These peaks are diagnostic of cellulose and hemicellulose and result from the C—O stretching in cellulose and hemicellulose.

Figure 6:
FIG. 6 is a representative scanning electron micrograph of biofuel produced in Example 4, according to the present invention.

The biofuel was examined using scanning electron microscopy (SEM). FIG. 6 shows the biofuel. The biofuel looks similar to the woody feedstock suggesting that the chemical reactions occurred without changing the physical appearance of the wood chip feedstock.

Figure 7:
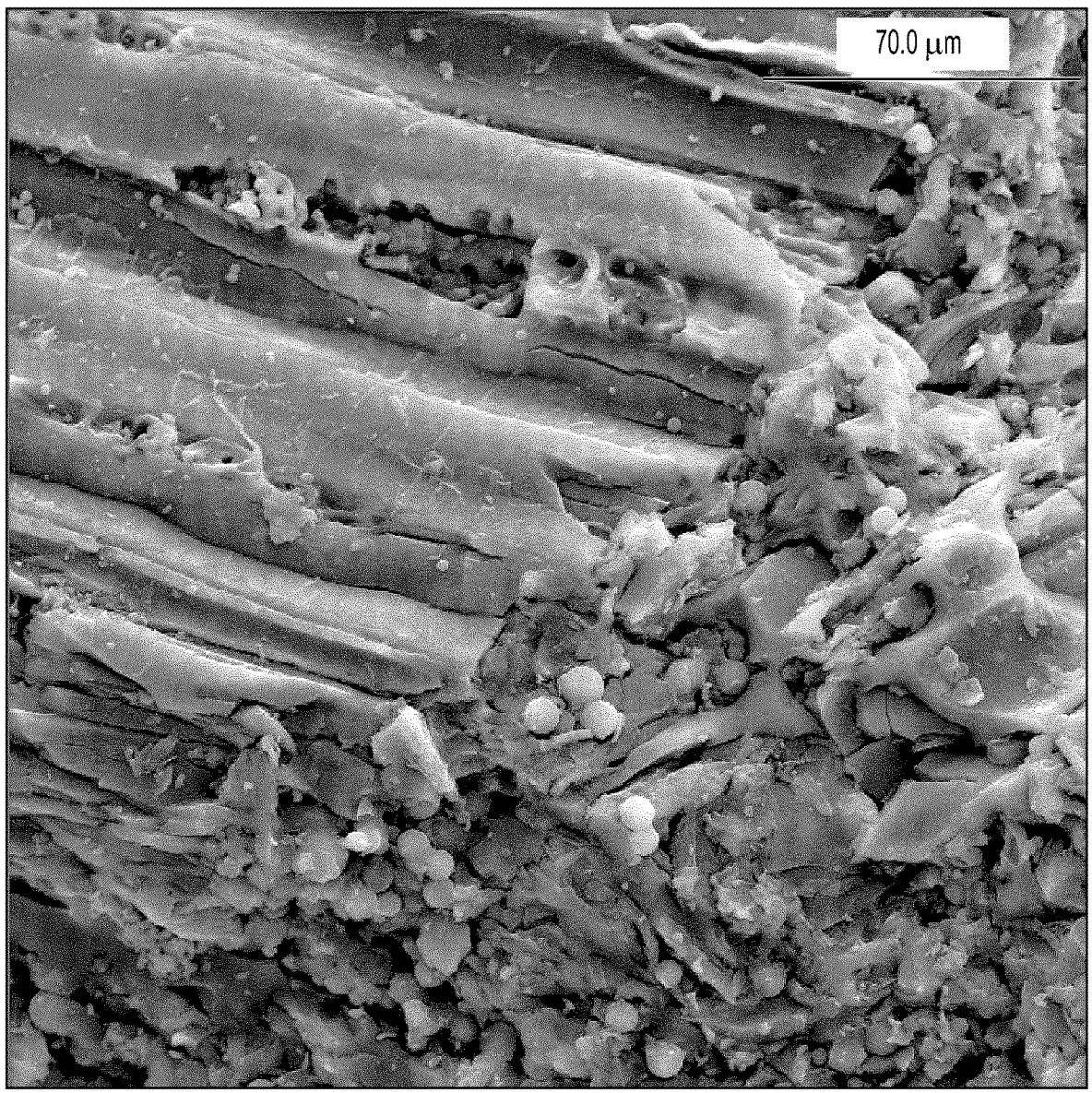
FIG. 7 is a representative scanning electron micrograph of biofuel produced using the method disclosed in U.S. Pat. No. 9,683,328.

FIG. 7 depicts the scanning electron micrograph of biofuel produced by the method disclosed in U.S. Pat. No. 9,683,328, incorporated herein by reference in its entirety, which is produced by an acidified slurry method. The SEM of the biofuel produced using the acidified slurry method has a woody structure with microspheres of the biofuel condensed onto it. The spheres are not present in the steam process. The differences between the scanning electron micrographs in FIG. 6 and FIG. 7 suggest that in the catalyzed steam hydrothermal carbonization process the reactions occur locally in the biomass, while in the acidified slurry process the reactions to form the biofuel occur in bulk solution forming microspheres of biofuel that condense on the biomass as evidenced in FIG. 7, and, in addition, plate out of solution onto the walls of the vessel.

It was surprising that in the reactions described using the acidified slurry process to produce biofuel disclosed in U.S. Pat. No. 9,683,328, apparently occur when the liquid phase is a thin layer on the biomass. As noted in FIG. 7, the microspheres indicate that the biofuel reaction is occurring in the bulk of the solution. In the steam process, as in the embodiments described herein, the reactions occur within the biomass so that the yield will be higher due to all the biofuel forming within the biomass. In contrast, the slurry process has a problem with the biofuel "plating out" on the walls of the reactor vessel leading to a buildup of material on the walls of the reactor vessel. Also, when the reaction occurs in solution the concentration of the intermediate reactants is lower and therefore the reaction is slower. Thus, the catalyzed steam process of the present invention provides surprising advantages to the production of biofuel.

Figure 8:
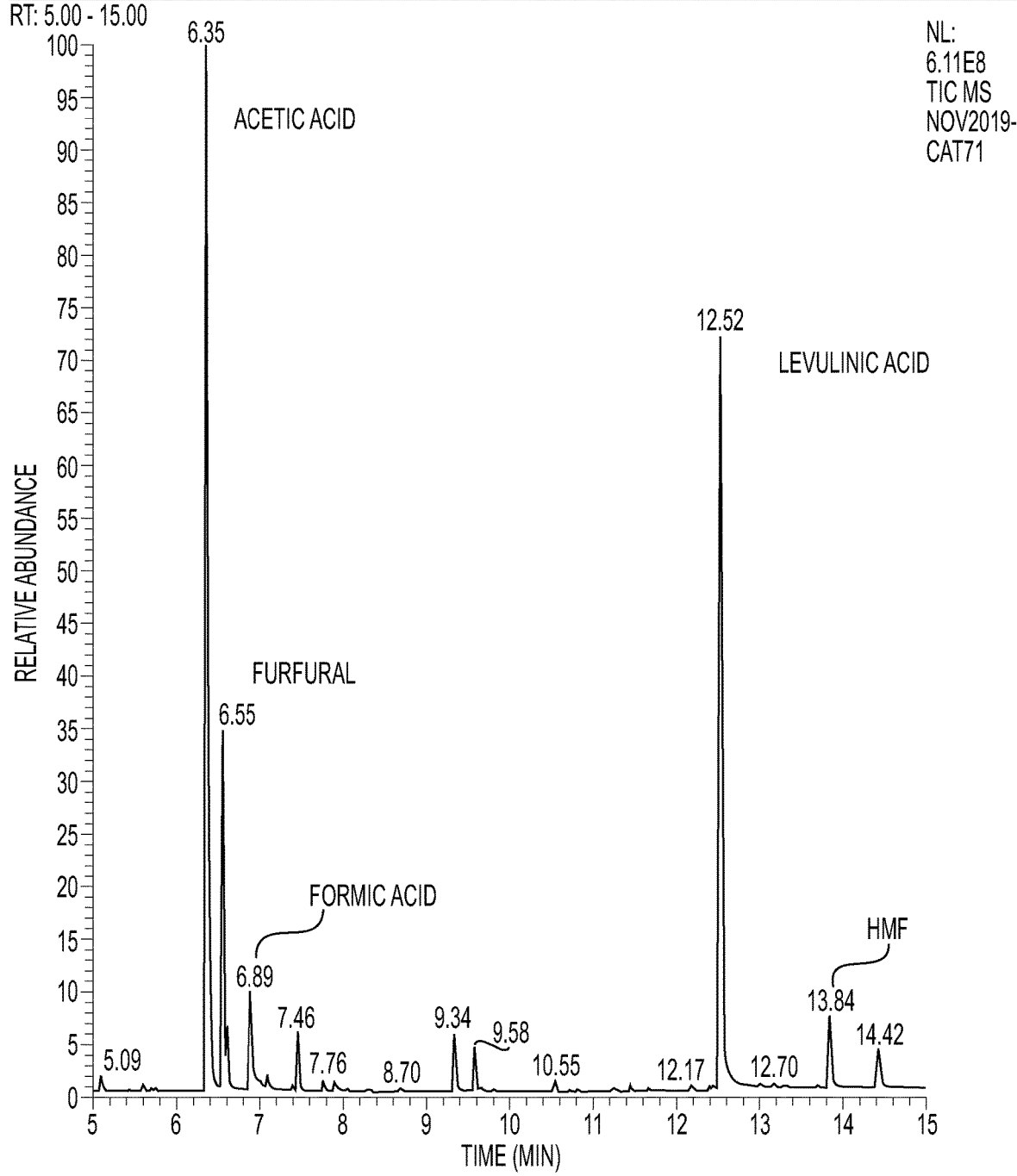
FIG. 8 is a representative chromatogram (Gas Chromatography/Mass Spectrometry) of the liquid portion product produced in Example 4, according to the present invention.

FIG. 8 depicts the chromatogram of the residual liquids in the reactor vessel after processing and cooling the vessel to room temperature. The chromatogram was acquired using a Thermo Focus gas chromatograph attached to a Thermo ISQ mass spectrometer. The two major components in solution were acetic acid and levulinic acid. The liquid also contained furfural, formic acid and HMF in lower quantities.

Example 5

Compares the Effect of Using a Catalyst to Not Using a Catalyst

Example 5 demonstrates the efficacy of using a volatile catalyst by comparing the HHV of the biofuel produced by processing the feedstock without catalyst with the HHV of the biofuel produced with a volatile catalyst. A 50-gram sample of green sapling wood (alder) was recovered from the forest and was sized to 6-10 mm pieces and placed in a basket suspended in a one litre pressure vessel. 50 ml of water was placed in the bottom of the pressure vessel. The pressure vessel was sealed. The pressure vessel was then heated to a temperature of about 240° C. and held at this temperature for thirty (30) minutes. After cooling the biofuel was removed from the pressure vessel and dried overnight at 70° C. A second 50-gram sample of the same feedstock was processed in exactly the same way except, instead of water in the bottom of the reactor vessel, 50 ml of 1 M maleic acid catalyst was used. The HHV of the no-catalyst condition was measured by bomb calorimetry to be 20.8 MJ/kg while the sample processed with a volatile catalyst was 23.9 MJ/kg. The HHV of the biofuel increased by 10% using a catalyst.

The biofuel reactor used for the production of polymeric solid biofuel from the hydrocarbonaceous feedstock as described above, can include other biomass suitable for biofuel production, and, as such, should not be construed in a limiting sense. The invention is intended to cover any adaptations or variations, or modifications of the present subject matter described herein.

It is to be understood that the present invention is not limited to the embodiments described above but encompasses any and all embodiments within the scope of the following claims.

We claim:

1. A method for producing a solid biofuel from hydrocarbonaceous feedstock, comprising the steps of:
   (a) loading a hydrocarbonaceous feedstock into a reactor vessel, the reactor vessel having a top and a bottom;
   (b) adding aqueous catalyst solution into the reactor vessel, wherein the catalyst solution resides at the bottom of the reactor vessel beneath the hydrocarbonaceous feedstock;
   (c) heating the reactor vessel to a temperature at or above 170° C. to catalyze reaction of the hydrocarbonaceous feedstock under saturated steam conditions for a time sufficient to yield polymeric biofuel; and
   (d) isolating the polymeric biofuel from the reactor vessel, wherein the hydrocarbonaceous feedstock is suspended above the bottom of the reactor vessel and is catalyzed by the aqueous catalyst solution under the saturated steam conditions.

2. The method for producing a solid biofuel from hydrocarbonaceous feedstock according to claim 1, wherein heating of the reactor vessel is for a heating time that ranges from about five (5) minutes to one hundred and eighty (180) minutes.

3. The method for producing a solid biofuel from hydrocarbonaceous feedstock according to claim 1, further comprising the step of: maintaining the reactor vessel at a pressure in a range of about 50 psi to 800 psi.

4. The method for producing a solid biofuel from hydrocarbonaceous feedstock according to claim 1, wherein the catalyst solution is an organic acid, wherein the organic acid comprises an acid selected from the group consisting of carbonic, acetic, formic, maleic, oxalic acids or a combination thereof.

5. The method for producing a solid biofuel from hydrocarbonaceous feedstock according to claim 1, wherein the catalyst solution is an inorganic acid selected from the group consisting of sulphuric, hydrochloric, hydrobromic, nitric and phosphoric acids and combinations thereof.

6. The method for producing a solid biofuel from hydrocarbonaceous feedstock according to claim 1, wherein the hydrocarbonaceous feedstock is selected from the group consisting of:
   wood, woodchips, sawdust, softwood, hardwood, decadent hemlock, beetle-killed pine, bark, forest cuttings, branches, leaves, birch, alder, balsam, cedar, pulp, paper, cardboard, plant biomass (including: water hyacinths, milfoil, algae, and including but not limited to, marine plants, algae, cyanobacteria), agricultural waste, greenhouse cuttings, straw, corn stover, food processing wastes, fruit and vegetable waste, animal waste, horse manure, cow manure, pig manure, municipal wastes, food waste, yard waste, coffee grounds, waste cardboard and waste paper.

7. The method for producing a solid biofuel from hydrocarbonaceous feedstock according to claim 1, wherein the yield of the polymeric biofuel is at least 20%.

8. A polymeric solid biofuel produced by a process comprising the steps of:
   (a) loading a hydrocarbonaceous feedstock into a reactor vessel, the reactor vessel having a top and a bottom;
   (b) adding aqueous catalyst solution into the reactor vessel, wherein the catalyst solution resides at the bottom of the reactor vessel beneath the hydrocarbonaceous feedstock;
   (c) heating the reactor vessel to a temperature at or above 170° C. to catalyze reaction of the hydrocarbonaceous feedstock under saturated steam conditions for a time sufficient to yield polymeric biofuel; and
   (d) isolating the polymeric biofuel from the reactor vessel, wherein the hydrocarbonaceous feedstock is suspended above the bottom of the reactor vessel and is catalyzed by the aqueous catalyst solution under the saturated steam conditions.

9. The polymeric solid biofuel according to claim 8, wherein a higher heating value of the polymeric biofuel is at least 20 MJ/Kg, and wherein a higher heating value (HHV) ratio of the hydrocarbonaceous feedstock to the polymeric biofuel is at least 20%.

10. A method for producing a solid biofuel from hydrocarbonaceous feedstock, comprising the steps of:
   (a) loading a hydrocarbonaceous feedstock into a reactor vessel, the reactor vessel having a top and a bottom;
   (b) introducing steam comprising a catalyst into the reactor vessel;

(c) heating the reactor vessel to a temperature at or above 170° C.to catalyze reaction of the hydrocarbonaceous feedstock under saturated steam steaming conditions for a time sufficient to yield polymeric biofuel; and (d) isolating the polymeric biofuel from the reactor vessel, wherein the hydrocarbonaceous feedstock is suspended above the bottom of the reactor vessel and is catalyzed by the introduction of the steam comprising the catalyst into the reactor vessel contacting the hydrocarbonaceous feedstock under the saturated steam conditions.

11. The method for producing a solid biofuel from hydrocarbonaceous feedstock according to claim 10, wherein the reactor vessel comprises a plurality of reactor vessels in communication with each other.

12. The method for producing a solid biofuel from hydrocarbonaceous feedstock according to claim 10, wherein the heating of the reactor vessel comprises a heating time in a range from and including 5 minutes to 180 minutes.

13. The method for producing a solid biofuel from hydrocarbonaceous feedstock according to claim 10, further comprising the step of: maintaining the reactor vessel at a pressure in a range of from about 50 psi to 800 psi.

14. The method for producing a solid biofuel from hydrocarbonaceous feedstock according to claim 10, wherein the catalyst is an organic acid.

15. The method for producing a solid biofuel from hydrocarbonaceous feedstock according to claim 14, wherein the organic acid comprises an acid selected from the group consisting of carbonic, acetic, formic, maleic, oxalic acids and combinations thereof.

16. The method for producing a solid biofuel from hydrocarbonaceous feedstock according to claim 10, wherein the catalyst comprises an inorganic acid.

17. The method for producing a solid biofuel from hydrocarbonaceous feedstock according to claim 16, wherein the inorganic acid comprises an acid selected from the group consisting of sulphuric, hydrochloric, hydrobromic, nitric and phosphoric acids and combinations thereof.

18. The method for producing a solid biofuel from hydrocarbonaceous feedstock according to claim 10, wherein the hydrocarbonaceous feedstock is selected from the group consisting of wood, woodchips, sawdust, softwood, hardwood, decadent hemlock, beetle-killed pine, bark, forest cuttings, branches, leaves, birch, alder, balsam, cedar, pulp, paper, cardboard, plant biomass (including: water hyacinths, milfoil, algae, and including but not limited to, marine plants, algae, cyanobacteria), agricultural waste, greenhouse cuttings, straw, corn stover, food processing wastes, fruit and vegetable waste, animal waste, horse manure, cow manure, pig manure, municipal wastes, food waste, yard waste, coffee grounds, waste cardboard and waste paper.

19. The method for producing a solid biofuel from hydrocarbonaceous feedstock according to claim 10, wherein a yield of the polymeric biofuel is at least 20%.

20. The method for producing a solid biofuel from hydrocarbonaceous feedstock according to claim 10, wherein a higher heating value of the polymeric biofuel is at least 20 MJ/Kg, and wherein a higher heating value (HHV) ratio of the hydrocarbonaceous feedstock to the polymeric biofuel is at least 20%.

21. A method for producing valuable organic chemicals from hydrocarbonaceous feedstock, comprising the steps of:

(a) loading a hydrocarbonaceous feedstock into a reactor vessel, the reactor vessel having a top and a bottom;

(b) introducing saturated steam comprising a catalyst into the reactor vessel;

(c) heating the reactor vessel to a temperature at or above 170° C.to catalyze reaction of the hydrocarbonaceous feedstock under saturated steam conditions for a time sufficient to yield polymeric biofuel; and (d) isolating a liquid containing the valuable organic chemicals produced by the reaction of the hydrocarbonaceous feedstock under the saturated steam conditions from the reactor vessel, wherein the valuable organic chemicals are selected from the group consisting of furfural, 2,5 hydroxymethyl furfuraldehyde, acetic acid, formic acid, and levulinic acid, and wherein the hydrocarbonaceous feedstock is suspended above the bottom of the reactor vessel and is catalyzed by the introduction of the steam comprising the catalyst into the reactor vessel contacting the hydrocarbonaceous feedstock under the saturated steam conditions.

22. An apparatus for producing biofuel, comprising:

a one reactor vessel configured for receiving a hydrocarbonaceous feedstock, the reactor vessel configured to enable a reaction of the hydrocarbonaceous feedstock under saturated steam conditions for a time sufficient to yield a polymeric biofuel, the reactor vessel having a top and a bottom;

a heater configured for heating the reactor vessel for the reaction, the heater being positioned in communication with the reactor vessel;

a lid positioned on the reactor vessel configured for opening and closing the reactor vessel to receive the hydrocarbonaceous feedstock into the reactor vessel and to remove from the reactor vessel the polymeric biofuel produced from the reaction; and a removable basket configured for holding the hydrocarbonaceous feedstock or the produced polymeric biofuel, the removeable basket being supported on a support above the bottom of the reactor vessel.

23. The apparatus for producing biofuel according to claim 22, further comprising: a plurality of reactor vessels in communication with each other, each of the plurality of reactor vessels having a said heater and a said lid.

24. The apparatus for producing biofuel according to claim 22, further comprising: a boiler chamber in communication with the reactor vessel configured to supply saturated steam and a catalyst into the reactor vessel for the reaction.

25. The apparatus for producing biofuel according to claim 22, further comprising: a chamber in communication with the reactor vessel for receiving the polymeric biofuel or other reaction product from the reactor vessel, the chamber including a condenser and a discharge port for discharging the polymeric biofuel or the other reaction product.

26. The apparatus for producing biofuel according to claim 25, further comprising: a container to collect the polymeric biofuel or the other reaction product discharged from the chamber.

\* \* \* \* \*

UNITED STATES PATENT AND TRADEMARK OFFICE
CERTIFICATE OF CORRECTION

PATENT NO. : 12,104,134 B2  
APPLICATION NO. : 17/924467  
DATED : October 1, 2024  
INVENTOR(S) : Glenn Aldon Mcrae et al.

It is certified that error appears in the above-identified patent and that said Letters Patent is hereby corrected as shown below:

In the Claims

Column 23, Line 3, Claim 10, "feedstock under saturated steam steaming conditions" should read --feedstock under saturated steam conditions--

Column 24, Line 23, Claim 22, "a one reactor vessel configured for receiving" should read --a reactor vessel configured for receiving--

Signed and Sealed this  
Twenty-sixth Day of November, 2024

Katherine Kelly Vidal  
*Director of the United States Patent and Trademark Office*